(12) United States Patent
Blischak (10) Patent No.: US 7,896,866 B1
(45) Date of Patent: Mar. 1, 2011

(54) SYSTEM AND METHOD FOR MAKING AN IMPLANTABLE PUMP THINNER

(75) Inventor: Brian R. Blischak, Allen, TX (US)

(73) Assignee: Advanced Neuromodulation Systems, Inc., Plano, TX (US)

(*) Notice: Subject to any disclaimer, the term of this patent is extended or adjusted under 35 U.S.C. 154(b) by 1200 days.

(21) Appl. No.: 11/531,344

(22) Filed: Sep. 13, 2006

Related U.S. Application Data (60) Provisional application No. 60/717,297, filed on Sep. 15, 2005.

(51) Int. Cl.
*A61K 9/22* (2006.01)
(52) U.S. Cl. .................................. 604/891.1
(58) Field of Classification Search ............... 604/93.01, 604/95.02, 95.03, 288.01, 891.1
See application file for complete search history.

(56) References Cited

U.S. PATENT DOCUMENTS

| 5,443,450 | A  | * | 8/1995  | Kratoska et al. ............ 604/141 |
| 5,551,849 | A  |   | 9/1996  | Christiansen |
| 6,280,416 | B1 |   | 8/2001  | Van Antwerp et al. |
| 6,652,510 | B2 |   | 11/2003 | Lord et al. |

* cited by examiner

*Primary Examiner* — Kevin C. Sirmons
*Assistant Examiner* — Bradley G Thomas, Jr.
(74) *Attorney, Agent, or Firm* — Christopher S. L. Crawford; Peter Lando; Melissa Acosta (57) ABSTRACT

In one embodiment, an implantable drug pump device comprises: a port for transferring infusate to the device; a collapsible reservoir for storing infusate received via the port; the port extending through a housing of the device and into the reservoir; the reservoir comprising a bottom surface that moves in relation to an amount of infusate in the reservoir; the bottom surface being connected to an extensible structure; and wherein when the reservoir is at least partially emptied of infusate, the reservoir is in a substantially collapsed state with the bottom surface being disposed above an interior surface of the port and the extensible structure surrounds a portion of the port that extends into the housing.

6 Claims, 6 Drawing Sheets

SYSTEM AND METHOD FOR MAKING AN IMPLANTABLE PUMP THINNER

RELATED APPLICATION

The present application claims the benefit of Provisional Patent Application Ser. No. 60/717,297, filed Sep. 15, 2005, entitled "SYSTEM AND METHOD FOR MAKING AN IMPLANTABLE PUMP THINNER," which is incorporated herein by reference.

TECHNICAL FIELD

The present application relates to implantable infusion devices, and in particular, to implantable infusion devices of reduced thickness.

BACKGROUND

Implantable infusion devices for delivering infusates allow a user to remain mobile while receiving therapy provided by the device. Modern implantable infusion devices commonly have a rigid housing that maintains a collapsible infusate reservoir. The housing includes a needle-penetrable septum that covers a infusate reservoir inlet port. A flow passage is provided between the infusate reservoir and an exterior surface of the device for delivery of infusate.

As with most implantable devices, it is desirable to minimize the size of implantable infusion devices to reduce inconvenience and irritation to a user. Advanced electronic circuits reduce the size of internal circuitry controlling implantable devices, and can reduce the size of power sources required to power the device. While circuitry advances have helped to minimize the size of implantable infusion devices, other components of the devices are often size-constraining. For example, the infusate reservoir inlet ports on implantable infusion devices may dictate the thickness of the device when they are stacked on top of the reservoir.

Reducing the size of the infusate reservoir inlet port faces certain constraints. When refilling an implantable infusion device, the septum covering the infusate reservoir inlet port is pierced with a needle and the infusate delivered to the infusate reservoir via the needle. The port dimensions perpendicular to the needle insertion direction must be large enough to ensure that the needle target can be located easily and the needle can be inserted without requiring multiple attempts at access. Also, the port must be deep enough parallel to the needle insertion direction to prevent the outlet of the needle from inadvertently coming out of the port during refilling and in turn delivering infusate to tissue surrounding the pump. Also, the thickness of the septum in the dimension along to the needle insertion direction must be great enough to ensure that a reliable seal is formed throughout the service life of the pump. Accordingly, modifications are constrained that reduce the height of the infusate reservoir inlet port and septum, thereby reducing the size of the implantable infusion device.

Furthermore, while it is desirable to minimize the overall size of an implantable infusion device, it is also desirable to maximize the size of the infusate reservoir relative to the total size of the implantable infusion device. Implantable infusion devices are generally refilled periodically via an infusate reservoir inlet port. While the refilling procedure is often minimally invasive for a user, it often requires a user to visit a healthcare facility or employ the services of a healthcare provider. Thus, if the size of the infusate reservoir is maximized, fewer refills would be necessary unless the drug stability is the factor limiting the period between refills. Smaller implantable infusion devices may be used, while minimizing the refill frequency, if the volumetric efficiency of the device is high. The volumetric efficiency refers to the total infusate capacity of the implantable infusion device compared to the total volume of the device.

Methods have been proposed to reduce the thickness of implantable infusion devices. U.S. Pat. No. 5,443,450 has a doughnut-shaped reservoir within a housing. The housing has a bulge near the top plate that allows the reservoir bellows to fully extend, thereby maximizing the capacity of the reservoir and minimizing the required thickness of the device. In U.S. Pat. Nos. 6,280,416 and 6,652,510 expandable polymeric bags and flexible diaphragms, respectively, are used to form infusate reservoirs, minimizing the required thickness of an associated implantable infusion device. Additionally, although all commercially available drug pumps utilize a central refill port, some designs have been proposed that place the fill port on the periphery of the pump. However, placement of the fill port on the periphery creates safety and other problems, because clinicians expect the fill port to be in the approximate center of the pump.

In some conventional solutions, a propellant gas such as a hydrocarbon, hydrofluorocarbon, chlorofluorocarbon, and/or similar compound, is used to pressurize an infusate reservoir. A reservoir may be positively pressurized with a propellant so that the reservoir pressure is greater than ambient pressure, or negatively pressured with a propellant so that the reservoir pressure is less than ambient pressure. Mechanical pressurization means may also be used. When propellants are used, the propellant chamber must be constructed of a material and in a manner that will inhibit the propellant from diffusing out of the propellant chamber. However, most polymeric materials have a measurable permeability that would allow propellant in vapor form to escape from the propellant chamber. Thus, the longevity of an implantable infusion device using propellant gas may be limited when polymeric materials are used to contain the propellant. Also, with the exception of the pump described in U.S. Pat. No. 5,443,450, devices using conventional reservoir shapes do not allow a port to protrude into space otherwise traversed by a collapsing or expanding reservoir, thereby requiring that the height of these devices be at least equal to the infusate reservoir inlet port height plus the reservoir thickness and increasing the overall height of those devices.

SUMMARY

The present application is generally directed to structures for reducing the thickness of an implantable infusion device. Certain embodiments allow an infusate reservoir to contour to the shape of an infusate reservoir inlet port that extends into the reservoir space. As infusate is removed from the infusate reservoir, extensible structures such as bellows and/or flexible diaphragms built into the reservoir allow the infusate reservoir volume to be reduced to a minimum by allowing the inner surfaces of the infusate reservoir to achieve their closest proximity to each other.

In one embodiment, an implantable drug pump device comprises: a port for transferring infusate to the device; a collapsible reservoir for storing infusate received via the port; the port extending through a housing of the device and into the reservoir; the reservoir comprising a bottom surface that moves in relation to an amount of infusate in the reservoir; the bottom surface being connected to an extensible structure; and wherein when the reservoir is at least partially emptied of infusate, the reservoir is in a substantially collapsed state with the bottom surface being disposed above an interior surface of the port and the extensible structure surrounds a portion of the port that extends into the housing.

The foregoing has outlined rather broadly certain features and/or technical advantages in order that the detailed description that follows may be better understood. Additional features and/or advantages will be described hereinafter which form the subject of the claims. It should be appreciated by those skilled in the art that the conception and specific embodiment disclosed may be readily utilized as a basis for modifying or designing other structures for carrying out the same purposes. It should also be realized by those skilled in the art that such equivalent constructions do not depart from the spirit and scope of the appended claims. The novel features, both as to organization and method of operation, together with further objects and advantages will be better understood from the following description when considered in connection with the accompanying figures. It is to be expressly understood, however, that each of the figures is provided for the purpose of illustration and description only and is not intended as a definition of the limits of the appended claims.

BRIEF DESCRIPTION OF THE DRAWINGS

FIGS. 3a-1, 3a-2, 3b-1, 3b-2, 3c-1, 3c-2, 3d-1, 3d-2, 3e-1, 3e-2, 3f-1, and 3f-2 are implantable infusion devices according to embodiments of the present invention.

DETAILED DESCRIPTION

Figure 1A:
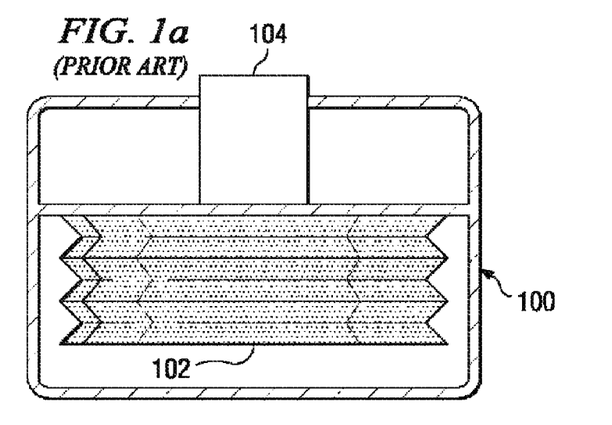
FIGS. 1a and 1b are, respectively, illustrations of a conventional implantable infusion device with an expanded and collapsed infusate reservoir.
Figure 1B:
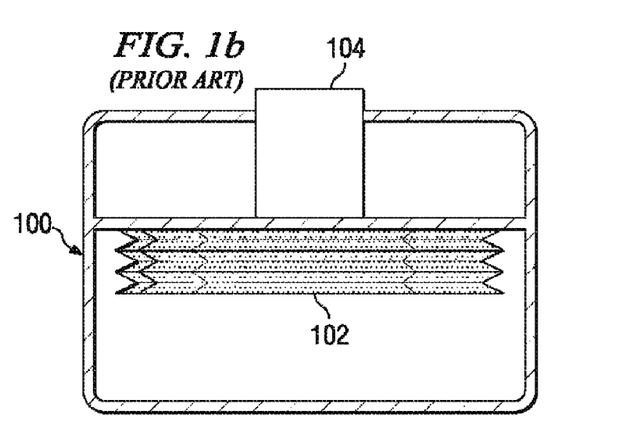

As mentioned above, the thickness of a conventional implantable infusion device is generally defined by the height of the infusate reservoir plus the height of the infusate reservoir inlet port. As shown in FIGS. 1a and 1b, conventional devices must have sufficient thickness to support an infusate reservoir 102 in both expanded (FIG. 1a) and collapsed (FIG. 1b) positions. The total height of the device 100 is defined by the height of the infusate reservoir 102 and the infusate reservoir inlet port 104.

Figure 2A:
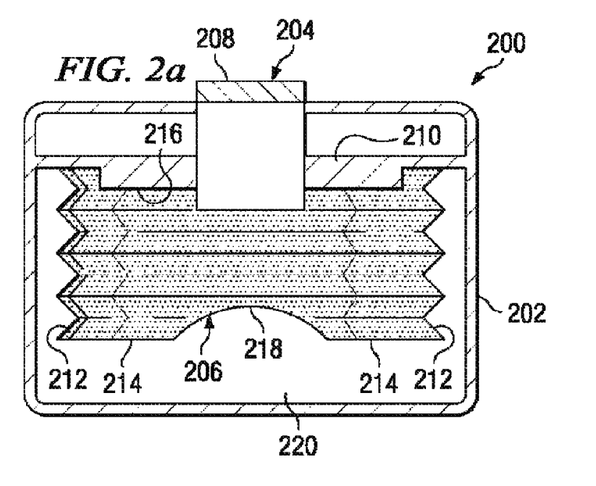
FIGS. 2a and 2b are, respectively, illustrations of an implantable infusion device according to an embodiment of the present invention with expanded and collapsed infusate reservoir.

FIG. 2a illustrates in cross-section an implantable infusion device 200 according to an embodiment of the present invention. Certain embodiments of the present invention generally operate to deliver infusate in a manner similar to that described in U.S. Pat. No. 6,620,151 to Blischak et al., incorporated herein by reference. That is, embodiments of the present invention generally comprise an infusate reservoir of sufficient volume so as to provide a supply of infusate over a desired flow period. The infusate is pressurized and driven from an infusate reservoir by a drive source. The drive source can be a two-phase fluid (or combination of fluids), which is confined between a housing of the device and a movable diaphragm structure, a drive spring that forms the diaphragm structure, or like mechanisms/structures that develop a known pressure. Infusate from an infusate reservoir is passed to a catheter having a distal end positioned at a site for infusate deliver.

In the embodiment shown in FIG. 2a, implantable infusion device 200 comprises housing 202. Implantable infusion device 200 in this embodiment is cylindrical in shape. In other embodiments, other pump shapes may be used, such as rectangular and oval pumps. Housing 202 is comprised of a durable, biocompatible material such as biocompatible metal or plastic. Metals such as titanium and titanium alloys are preferably used. Certain embodiments of the present invention use a biocompatible material for housing 202 that is constructed to have at least a portion that is resiliently flexible. Like housing 202, other tissue-contacting or drug-contacting components of implantable infusion device 200 are also comprised of biocompatible materials such as titanium and titanium alloys, ceramics, glass, and other metal alloys. Low permeability polymers may also be used in certain embodiments.

Implantable infusion device 200 further comprises infusate reservoir inlet port 204. Infusate reservoir inlet port 204 extends from an external surface of housing 202, and provides a fluid path from septum 208 into infusate reservoir 206. Infusate reservoir inlet port 204 comprises septum 208 that covers port 204. Septum 208 is constructed of a pierceable, resilient, biocompatible material such as silicone or rubber. Materials used for septum 208 are preferably selected to allow a needle to penetrate and be withdrawn from septum 208 without compromising the septum's resistance to leakage from infusate present in port 204 and infusate reservoir 206. Certain embodiments of the present invention comprise an electronic capsule 210. Electronics capsule 210 comprises electronic circuitry and/or power sources for operating implantable infusion device 200. The electronics capsule is hermetically sealed in embodiments of the present invention. In other embodiments, electronics capsule 210 may be located externally from the housing.

Infusate reservoir 206 is shown in expanded form in FIG. 2a. Infusate reservoir 206 is bounded by top plate 216, bottom plate 214, and bellows 212. Infusate reservoir 206 is comprised of materials selected to not degrade or affect the stability of any infusates that will be contained by infusate reservoir 206. Surrounding infusate reservoir 206 is a propellant chamber 220. Propellant chamber is comprised of materials selected to have a low permeability to vapor and/or liquid phase propellant contained by the propellant chamber. In certain embodiments of the present invention, the position, capacity, and materials of infusate reservoir 206 and propellant chamber vary and are selected to optimize the operation of the device for a particular application or applications.

Top plate 216 of infusate reservoir 206 is attached to housing 202 on each end and to the sides of infusate reservoir inlet port 204. Infusate reservoir inlet port 204 extends through top plate 216 into infusate reservoir 206. In this embodiment of the present invention, bottom plate 214 comprises a single flexible dome-like convolution 218. In other embodiments, the convolution could be shaped differently than shown, such as ring-shaped with a generally flat section inside the ring. Flexible convolution 218 is aligned with an axis of infusate reservoir inlet port 204. Top plate 216 and bottom plate 214 are connected by bellows 212 formed of a plurality of convolutions. In other embodiments, more or fewer convolutions form bellows 212. A plurality of ports, bellows, convolutions, diaphragms, and/or reservoirs are used in certain embodiments of the present invention to maximize volumetric efficiency, reservoir capacity, and provide the ability to infuse more than one infusate from a single implantable infusion device.

Figure 2B:
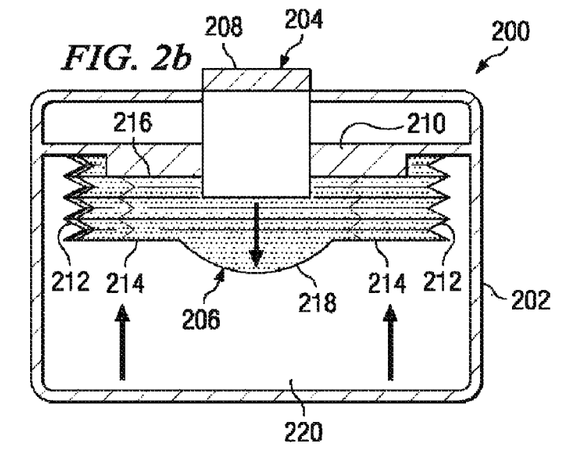

Infusate reservoir 206 is shown in collapsed form in FIG. 2b. As infusate is removed from infusate reservoir, bottom plate 214 moves towards top plate 216, collapsing bellows 212. Single flexible convolution 218 is pushed downwards as it contacts the infusate reservoir inlet port as bottom plate 214 moves towards top plate 216. In this manner, bottom plate 214 and top plate 216 can come in closer contact, minimizing the amount of dead volume in infusate reservoir 206 and, in turn, generally increasing the usable volume. Infusate reservoir inlet port 204 may comprise a needle stop comprised of a durable material such as polymer or metal to prevent needles from puncturing the back or side of infusate reservoir inlet port 204, and to prevent excessive damage to the needle tip when contacting it.

FIGS. 3a-1, 3a-2, 3b-1, 3b-2, 3c-1, 3c-2, 3d-1, 3d-2, 3e-1, 3e-2, 3f-1, and 3f-2 illustrate additional embodiments of the present invention. While each of these FIGURES present individual embodiments of the invention, one of ordinary skill in the art will recognize that additional embodiments can be employed according to appropriate modifications, e.g., using various combinations of the features presented in these figures.

Figure 3A:
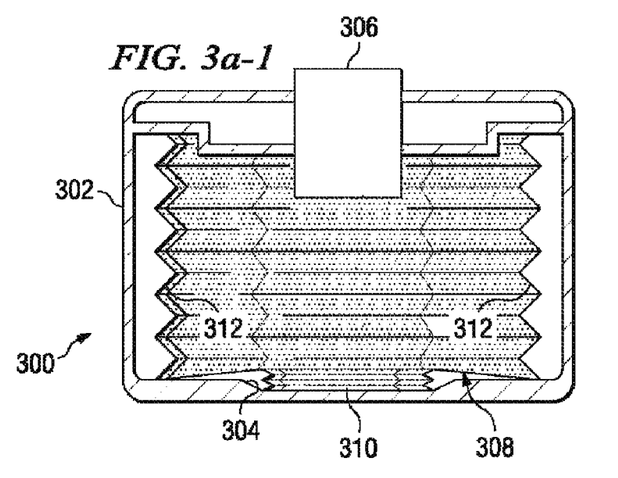
Figure 3A:
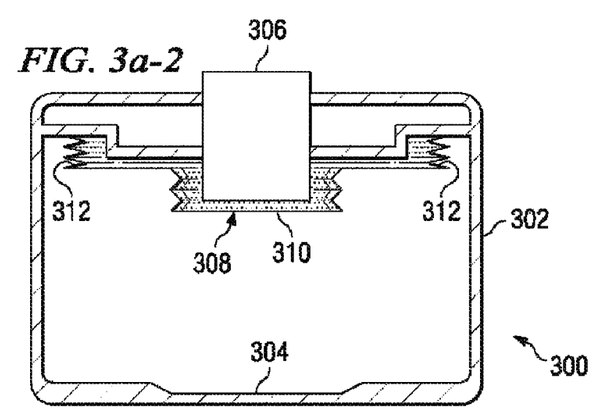
Figure 3B:
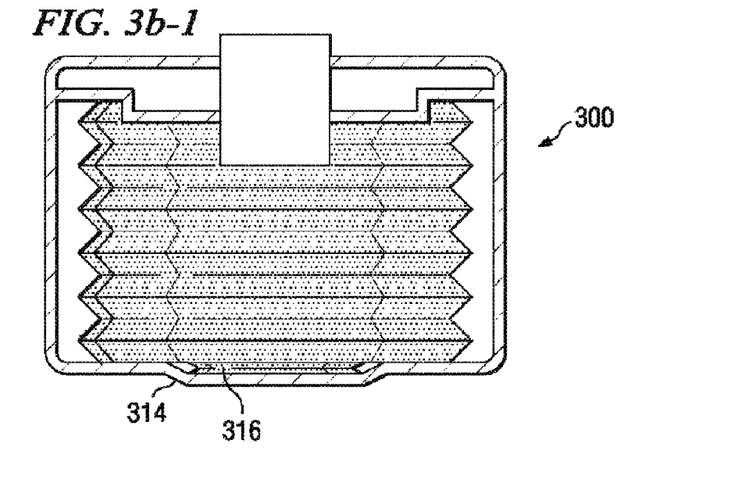

In FIGS. 3a-1 and 3b-1, implantable infusion device 300 comprises housing 302 with a bottom portion comprising a thin, circular central area 304 aligned with an axis of infusate reservoir inlet port 306. This thicker portion of housing 302 bottom surrounding central area 304 provides additional stiffness for use with some propellants and/or materials used with embodiments of the present invention. Central area 304 forms a recess on the internal side of housing 302 to enable bellows 312 to extend more fully. Not all embodiments comprise a recess as shown in FIGS. 3a-1 and 3b-1.

Implantable infusion device 300 comprises an infusate reservoir 308 with a lower bottom plate comprising a second bellows 310. In certain embodiments, second bellows comprises one or more convolutions. When infusate reservoir 308 is full, second bellows 310 is collapsed and fits into the recess formed by central area 304, while the first bellows 312 is expanded. When infusate reservoir 308 is empty, the second bellows expands to allow infusate reservoir to collapse around infusate reservoir inlet port 306, and for first bellows 312 to collapse. By allowing the infusate reservoir 308 to collapse more completely and expand more completely, the infusate reservoir's capacity and the implantable device's volumetric efficiency is maximized. In preferred embodiments of the present invention, the infusate reservoir is pressurized using a two-phase propellant present in the space between the infusate reservoir 308 and the housing 302. It is also noted in regard to these embodiments that it is also possible to reverse the position of the propellant and the infusate, e.g., the propellant can be placed inside the bellows and the infusate within the annular space or in one or several secondary containers within the annular space.

Figure 3B:
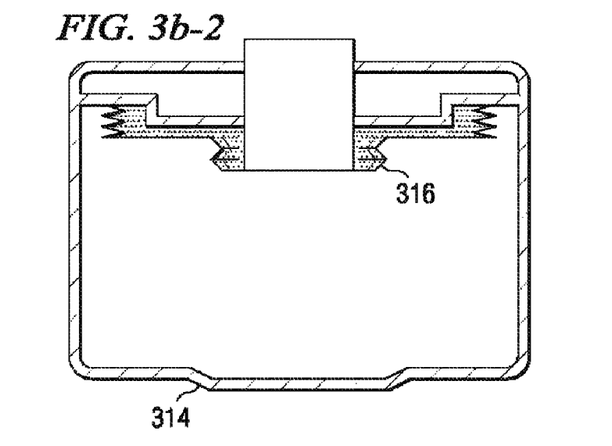
Figure 3C:
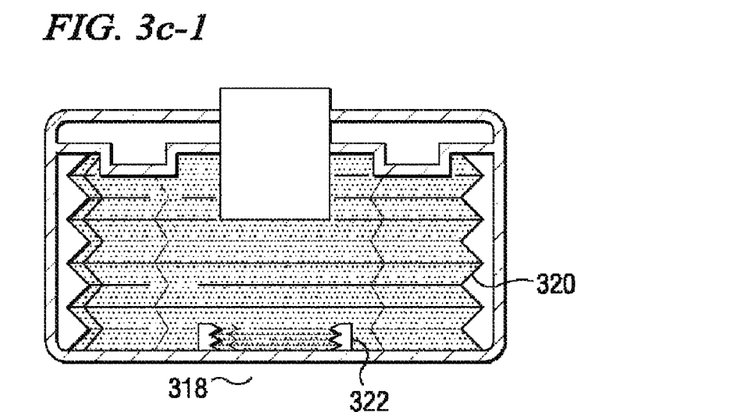
Figure 3C:
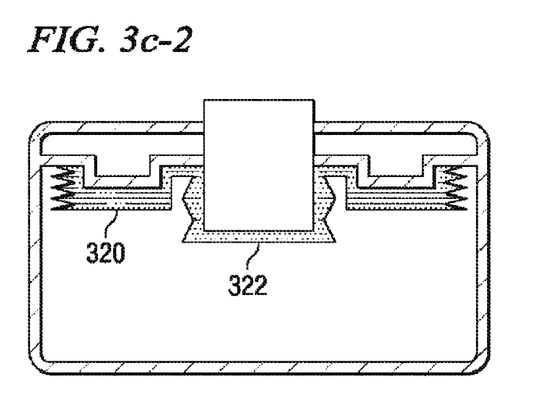

FIGS. 3b-1 and 3b-2 shows an implantable infusion device comprising a housing with central area 314 that contains a bulge. Central area 314 of the housing bulges outward from the exterior of the housing, thus allowing collapsed secondary bellows 316 to fit into the interior portion of the bulge when the infusate reservoir is full.

FIGS. 3c-1 and 3c-2 depicts implantable drug pump according to an embodiment of the present invention. The bottom surface 318 of the device housing is substantially uniform and, accordingly, does not include a recess to accommodate the collapsed secondary bellows. As shown in FIGS. 3b-1 and 3b-2, the lower portion 322 of the primary bellows to adapted to accommodate the secondary bellows thereby allowing the bottom surface of the primary bellows to contact the housing of the device when the reservoir is filled with infusate.

Figure 3D:
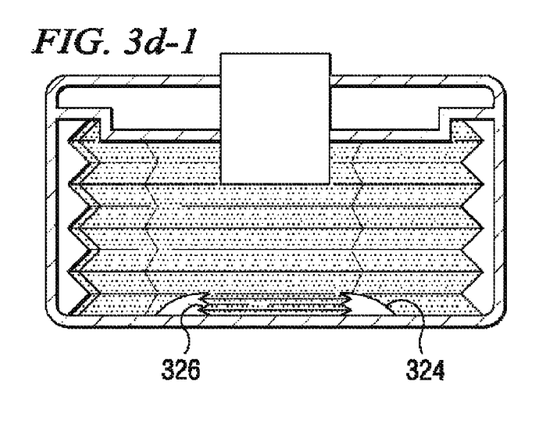
Figure 3D:
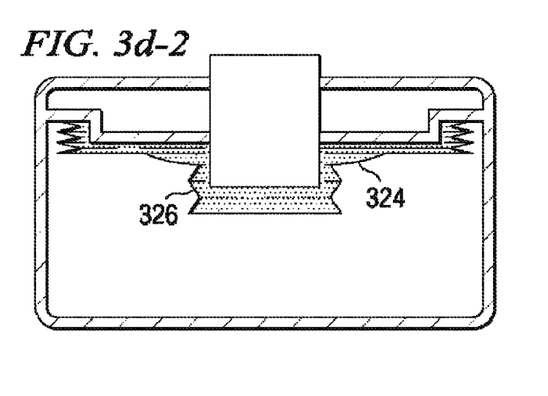
Figure 3E:
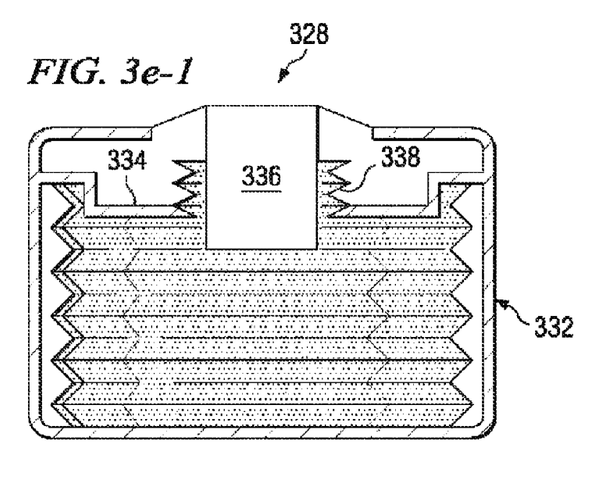
Figure 3E:
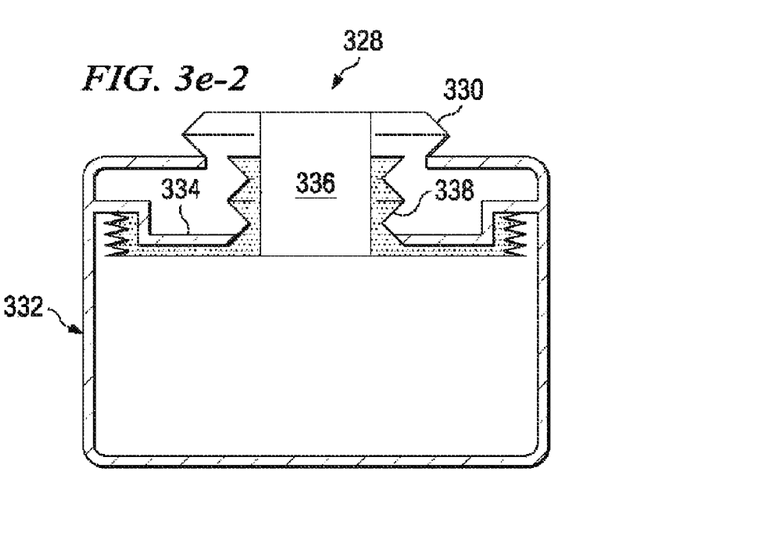

FIGS. 3d-1 and 3d-2 depict an embodiment comprising a lower plate with convolution 324 that allows secondary bellows 326 to be displaced upwards when the infusate reservoir is filled. In this embodiment, a recess or flexible central area is not used to accommodate the collapsed secondary bellows 326. Convolution 324 may comprise half and full convolutions. In certain embodiments of the present invention, other mechanisms to allow secondary bellows 326 to be displaced upwards, such as hinges, may also be used.

FIGS. 3e-1, 3e-2, 3f-1, and 3f-2 illustrate embodiments where an infusate reservoir inlet port is displaceable in relation to the housing of an implantable infusion device using convolutions or bellows on the housing. In the embodiment of FIGURE housing top 332 comprises convolutions 330 that allow central portion 328 to be displaced upwards when the infusate reservoir is in a collapsed state. The infusate reservoir also comprises secondary bellows 338 that maintains top plate 334 seal around the infusate reservoir inlet port 336 as the infusate reservoir volume changes. As the infusate reservoir collapses as infusate is removed, infusate reservoir inlet port 336 is displaced upwards.

Figure 3F:
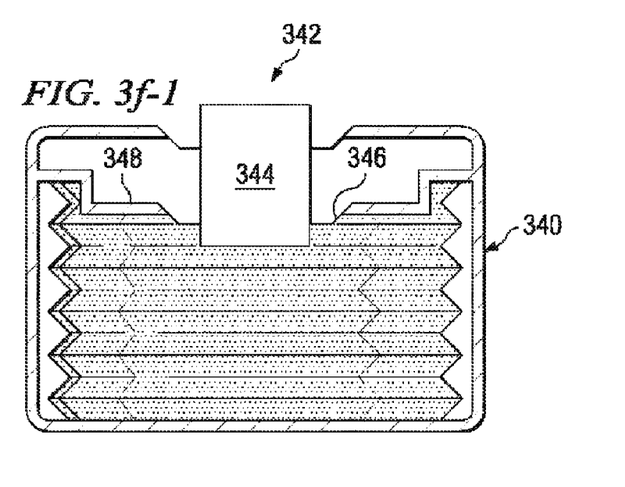
Figure 3F:
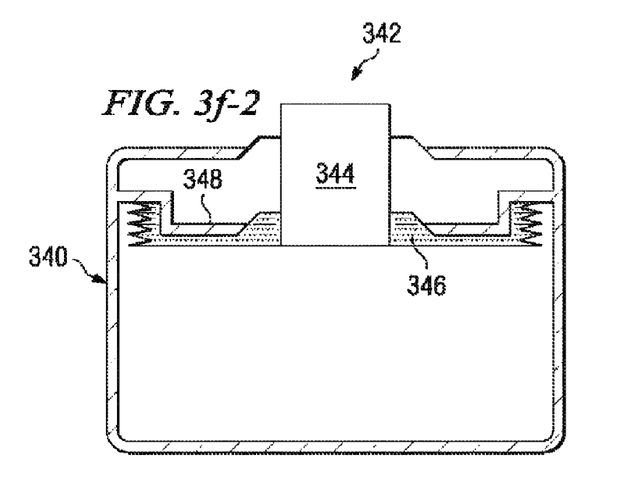

In the embodiment of FIGS. 3f-1 and 3f-2, a half convolution 342 is used on housing top 340 allowing infusate reservoir inlet port 344 to be displaced upwards when the infusate reservoir is empty and collapsed. A convolution 346 is also present on top plate 348 allowing infusate reservoir inlet port 344 displacement.

A benefit of the embodiments shown in FIGS. 3e-1, 3e-2, 3f-1, and 3f-2 is that the position of the infusate reservoir inlet port can be used to indicate the volume of infusate present in the infusate reservoir, either by palpitation of the site at which implantable infusion device is located, or by electronically sensing the position of the port using sensors known to those of ordinary skill in the art. Additionally, a displaced infusate reservoir inlet port can aid when refilling the infusate reservoir by making the port easier to find. Also, drug diversion can be discouraged by making the port harder to find when the infusate reservoir is full.

In certain implantable infusion device designs, the infusate reservoir is continually under pressure. Accordingly, certain embodiments of the invention, such as those shown in FIGS. 3e-1, 3e-2, 3f-1, and 3f-2, may use a mechanism to resist the tendency of the infusate reservoir inlet port to displace when the infusate reservoir is under pressure. In the embodiments shown in FIGS. 3e-1, 3e-2, 3f-1, and 3f-2, the spring constants of the convolutions may be selected to counter this displacing force. In other embodiments of the present invention, force generated using magnetic or electrical devices may be applied to the infusate reservoir inlet port using means known to those of ordinary skill in the art using, for example, impedence coils, electromagnets, etc. A mechanical lock could also be used to hold the infusate reservoir inlet port in place until a predetermined infusate reservoir volume is reached, releasing the port and thus indicating that the infusate reservoir should be refilled.

In yet other embodiments, the infusate reservoir inlet port is attached to the lower plate of the infusate reservoir. In these embodiments, as the lower plate moves towards the upper plate as the infusate reservoir is emptied, the infusate reservoir inlet port would displace outward as with the embodiments shown in FIGS. 3e-1, 3e-2, 3f-1, and 3f-2.

In certain embodiments, a plurality of infusate reservoirs are used. To fill each infusate reservoir, a single septum may be used and the infusate reservoir inlet port is divided into two separate loading ports. In these embodiments, different infusates can be present in each of the plurality of infusate reservoirs and either mixed before infusion, or kept separate and infused using different infusion outlets. Various configurations of reservoirs can be used to keep the reservoirs separate from each other. The plurality of reservoirs can share common components such as a common top or bottom plate.

Additionally, the locations of the infusate and the propellant can be reversed (i.e., the propellant can be placed within the bellows and the infusate can be placed between the bellows and the housing). Such a reversal can be accomplished by employing a conduit between the inlet port and the area between the bellows and the housing.

Although representative embodiments and advantages have been described in detail, it should be understood that various changes, substitutions and alterations can be made herein without departing from the spirit and scope of the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods, or steps.

What is claimed is:

1. An implantable drug pump device for providing infusate to a patient, comprising:
    a housing;
    a refill port for transferring infusate into the device, the refill port extending through the housing into an interior space of the housing;
    a septum within the refill port for sealing the refill port and for receiving a needle;
    a reservoir for storing infusate within the housing, wherein the reservoir comprises a top plate, a bottom plate, and a bellows connecting the top plate and the bottom plate, wherein the bellows expands when infusate is provided through the refill port and the bellows collapses upon discharge of infusate from the reservoir; and
    an extensible structure connected to the bottom plate of the reservoir, wherein (i) the extensible structure is substantially collapsed when the bellows is substantially expanded, and (ii) the extensible structure is substantially expanded away from the bottom plate when the bellows is substantially collapsed;
    wherein, when the reservoir is substantially empty, (i) the bottom plate of the reservoir is disposed above a portion of the refill port that is disposed farthest within the interior space of the housing and (ii) the extensible structure extends about the refill port.

2. The implantable drug pump device of claim 1 wherein the extensible structure comprises a bellows.

3. The implantable drug pump device of claim 1 wherein the extensible structure comprises a convolution structure.

4. The implantable drug pump device of claim 1 wherein the extensible structure comprises a bellows and a convolution structure.

5. The implantable drug pump device of claim 1 wherein the housing comprises a recess to accommodate the extensible structure in a collapsed state when the reservoir is expanded.

6. The implantable drug pump device of claim 1 wherein the bottom plate comprises an indention to accommodate the extensible structure in a collapsed state when the reservoir is expanded.

* * * * *